(12) United States Patent
Assie et al.

(10) Patent No.: US 7,523,821 B2
(45) Date of Patent: Apr. 28, 2009

(54) DISPOSABLE PACKAGE FOR LIQUID, PASTY OR POWDER PRODUCT

(75) Inventors: Jean-Louis Assie, Bergerac (FR); Bernard Pauchet, Saint Capraise de Lalinde (FR)

(73) Assignee: Taiki Corporation, Ltd., Osaka (JP)

( * ) Notice: Subject to any disclaimer, the term of this patent is extended or adjusted under 35 U.S.C. 154(b) by 411 days.

(21) Appl. No.: 10/539,266

(22) PCT Filed: Dec. 17, 2003

(86) PCT No.: PCT/FR03/03761

§ 371 (c)(1), (2), (4) Date: Jun. 16, 2005

(87) PCT Pub. No.: WO2004/056345

PCT Pub. Date: Jul. 8, 2004

(65) Prior Publication Data

US 2006/0163101 A1 Jul. 27, 2006

(30) Foreign Application Priority Data

Dec. 17, 2002 (FR) .................................. 02 15971

(51) Int. Cl.
*B65D 75/00* (2006.01)

(52) U.S. Cl. ........................ 206/204; 206/207; 206/484; 206/812; 15/104.93

(58) Field of Classification Search .................. 206/210, 206/438, 440, 205, 207, 812, 484, 204, 484.1, 206/823, 581; 15/104.93, 104.94

See application file for complete search history.

(56) References Cited

U.S. PATENT DOCUMENTS

| 2,817,336 A | | 12/1957 | Kravitz et al. |
| 3,053,255 A | | 9/1962 | Meyer |
| 3,580,254 A | | 5/1971 | Stuart |
| 3,635,567 A | * | 1/1972 | Richardson, Jr. ............. 401/132 |
| 3,826,259 A | | 7/1974 | Bailey |
| 4,696,393 A | * | 9/1987 | Laipply ....................... 206/210 |
| 4,762,124 A | * | 8/1988 | Kerch et al. .................. 604/307 |
| 4,808,172 A | | 2/1989 | Murata |
| 4,858,604 A | | 8/1989 | Konishi |
| 4,881,278 A | * | 11/1989 | Farah .......................... 4/245.1 |
| 4,935,158 A | * | 6/1990 | Aszman et al. ........... 15/104.93 |
| 5,111,934 A | * | 5/1992 | Morin ......................... 206/229 |
| 5,271,940 A | | 12/1993 | Cleary et al. |
| 5,320,217 A | * | 6/1994 | Lenarz ........................ 206/209 |
| 5,487,932 A | * | 1/1996 | Dunshee ....................... 428/68 |
| 5,511,689 A | | 4/1996 | Frank |
| 5,562,642 A | * | 10/1996 | Smith et al. ................. 604/289 |
| 6,086,912 A | | 7/2000 | Gilman |

(Continued)

FOREIGN PATENT DOCUMENTS

EP 0 368 408 5/1990

(Continued)

*Primary Examiner*—Jacob K Ackun, Jr.
(74) *Attorney, Agent, or Firm*—Richard M. Goldberg

(57) ABSTRACT

Packaging for packaging a substance in a leakproof protective cover includes a protective cover having two parts of separable leakproof material containing an applicator fixed to the inside face of one of the two parts. A portion of fiber, sponge, or analogous structure in which the substance is distributed is contained within the applicator.

8 Claims, 2 Drawing Sheets

U.S. PATENT DOCUMENTS

| | | | | |
|---|---|---|---|---|
| 6,094,766 | A * | 8/2000 | Nash et al. | 15/104.93 |
| 6,446,795 | B1 * | 9/2002 | Allen et al. | 206/210 |
| 6,547,468 | B2 * | 4/2003 | Gruenbacher et al. | 401/133 |
| 6,607,514 | B2 * | 8/2003 | Reese | 604/289 |
| 6,695,515 | B1 | 2/2004 | Fleury | |
| 6,811,338 | B1 * | 11/2004 | Manske, Jr. et al. | 401/7 |
| 6,823,649 | B1 | 11/2004 | Pauchet | |
| 7,108,440 | B1 * | 9/2006 | Gruenbacher et al. | 401/132 |
| 7,163,101 | B2 * | 1/2007 | Harper | 206/210 |
| 7,240,790 | B2 * | 7/2007 | Wendel et al. | 206/210 |
| 2002/0011424 | A1 * | 1/2002 | Wilkman | 206/210 |
| 2003/0097725 | A1 * | 5/2003 | Smith | 15/104.93 |
| 2003/0106812 | A1 * | 6/2003 | Wilkman | 206/210 |
| 2003/0121116 | A1 * | 7/2003 | Keck et al. | 15/104.94 |
| 2003/0121530 | A1 * | 7/2003 | Borgonjon et al. | 134/6 |

FOREIGN PATENT DOCUMENTS

| | | |
|---|---|---|
| EP | 1 040 824 | 10/2000 |
| FR | 2801179 A1 | 5/2001 |
| WO | 94/09735 A1 | 5/1994 |

* cited by examiner

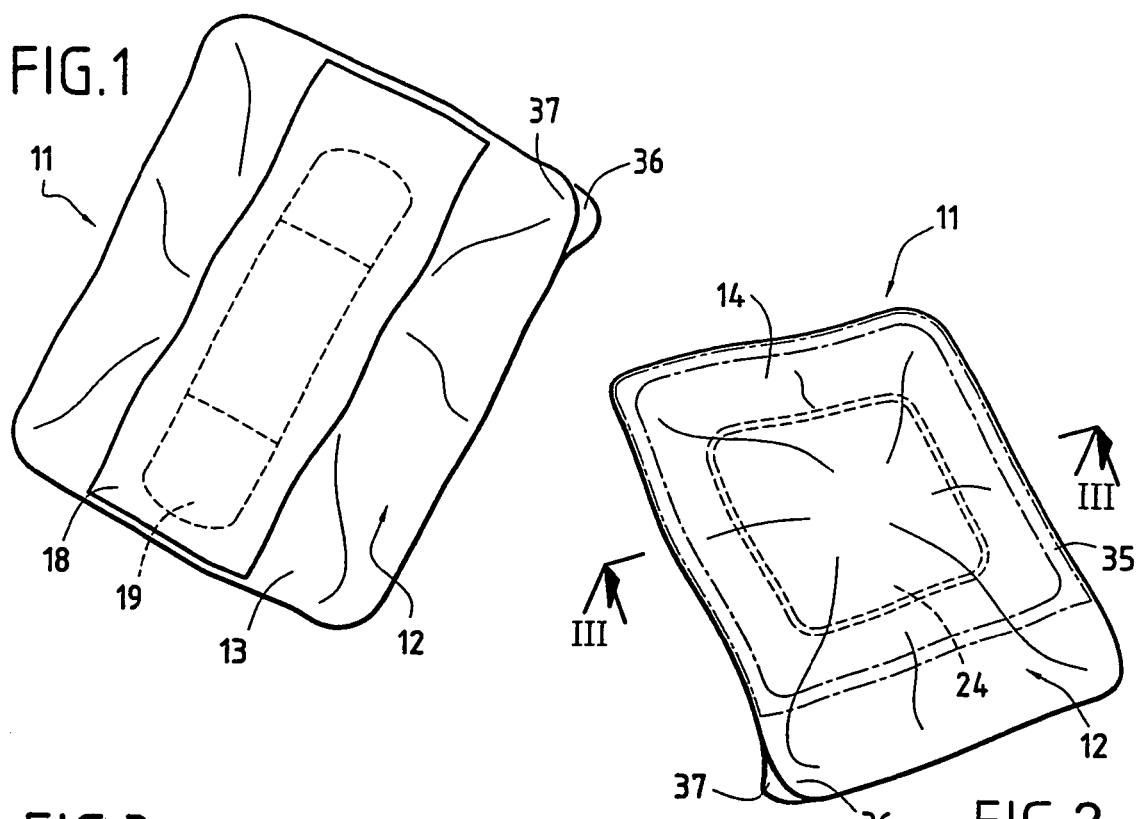
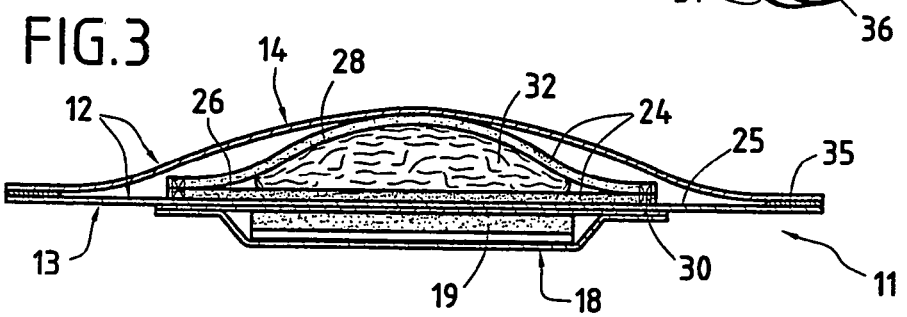
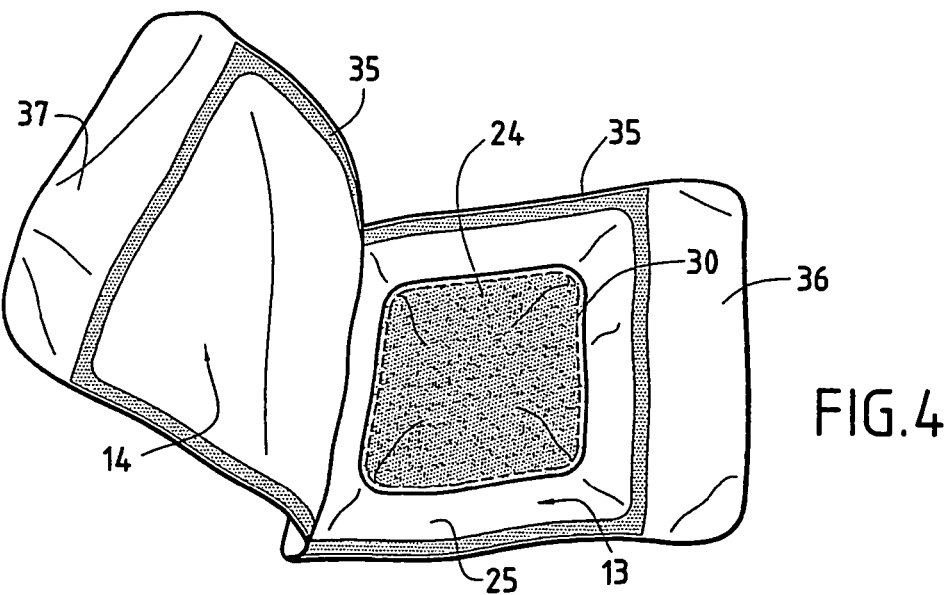

DISPOSABLE PACKAGE FOR LIQUID, PASTY OR POWDER PRODUCT

BACKGROUND OF THE INVENTION

The invention relates to single-use packaging for a liquid, semiliquid, or powder substance. The invention makes it easier in particular to apply a cosmetic, medical, or antiseptic composition, and more particularly any composition for application to the skin.

When traveling or engaging in sport, it can be desirable to have a cosmetic, medical, or antiseptic substance available that is packaged for use on a single occasion, with packaging being discardable after use.

For example, pieces of toweling soaked in eau de cologne or the like are known that are packaged between two sheets of flexible leakproof material. The user needs to extract the toweling from the leakproof pouch after opening it. The pouch therefore needs to be handled in order to be used. That concept is therefore not suitable for being transposed to packaging any kind of substance.

SUMMARY OF THE INVENTION

The invention relates to packaging enabling any kind of substance to be packaged, including a greasy cosmetic or a substance having a medical or an antiseptic effect that must not be touched by the fingers when it is deployed.

The invention provides single-use packaging for a liquid, semiliquid, or powder substance, the packaging comprising a protective cover comprising two separable leakproof pieces of material and an applicator enclosed in said protective cover, the packaging being characterized in that said applicator is fixed to the inside face of one of said parts, in that it comprises a portion of fiber, sponge, or analogous structure, and in that said substance is distributed in said structure.

The first advantage that results from this novel structure is that once the protective cover has been opened it itself facilitates application, and there is no risk of the user covering the fingers in the substance in question.

For example, the applicator may comprise a piece of flexible and porous material fixed via its periphery to said inside face. This piece of porous material may typically be material of the non-woven type. To increase the quantity of substance that can be retained in the structure of the applicator, a piece of cotton wool or the like may provided containing the substance and housed between said piece of flexible and porous material and said inside face.

In a presently preferred embodiment, the above-mentioned cover is made of two flexible and leakproof parts, typically obtained from sheets of laminated-together plastics and metal materials. The two parts are united by a close-outline junction line surrounding the location of the applicator. Consequently, when the packaging is offered to the user, the applicator is fully enclosed inside the leaktight protective cover.

According to another advantageous characteristic, when the above-defined packaging contains a dose of disinfectant or treatment substance for application to a wound or to a burn, the package is associated with an adhesive dressing. More precisely, a peel-off cover containing said adhesive dressing is fixed via one of its faces to an outside face of the protective cover. Consequently, after applying the substance, the user does not need to search through other equipment to find an adhesive dressing for protecting a wound, since the dressing is available on the packaging itself. In order to ensure that the dressing can be applied very easily, and possibly with one hand only, the outside face of said dressing is weakly secured to the inside face of the portion of the peel-off cover that is not fixed to the protective cover. That type of dressing is known in itself and is described in U.S. Pat. No. 5,511,689, but the fact of making it available on the packaging makes it easier to use.

BRIEF DESCRIPTION OF THE DRAWINGS

The invention appears more clearly in the light of the following description of a presently preferred embodiment of single-use packaging applying the principle of the invention, given purely by way of example and made with reference to the accompanying drawings, in which:

FIG. 1 is a diagrammatic perspective view of packaging in accordance with the invention;

FIG. 2 is a view showing the underside of FIG. 1;

FIG. 3 is a section view on III-III of FIG. 2;

FIG. 4 is a view of the packaging once open, ready for use;

DETAILED DESCRIPTION

Figure 5:
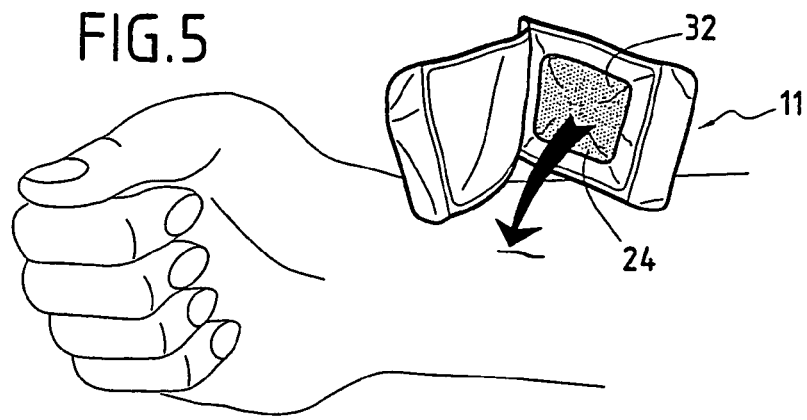
FIG. 5 shows an applicator being implemented on a wound.

The single-use packaging 11 as made available to the user is externally in the form of a cover 12 referred to herein as a "protective cover" made up of two separable parts of leakproof material 13, 14. When used for applying a disinfectant substance or the like, said protective cover carries another cover 18 on one of its faces, which other cover can be peeled off and retains an adhesive dressing 19. The features of this peel-off cover and of the dressing are described below. This is merely an option and does not mean that when the substance contained in the packaging is for treating a wound or a burn it must necessarily subsequently be protected by said dressing.

The cover 12 contains an applicator 24 which is fixed to the inside face 25 of one of the two parts of leakproof material. The applicator includes a portion of fiber, sponge, or similar structure and the treatment substance is distributed within said structure.

In the example shown, the applicator 24 comprises a piece of flexible and porous material 28 having its periphery fixed to the inside face 25. This piece 28 is taken from a sheet of non-woven type material presenting all of the qualities needed for applying the substance. Preferably, the non-woven material is based on cotton, of the fluffless type. In the example shown, a piece of cotton wool 32 or the like also containing the substance is housed between said piece of flexible and porous material 28 and said inside face 25.

In the embodiment descried specifically, the applicator forms a pouch holding captive the piece of cotton wool or the like. The pouch comprises another piece of flexible material 26 having its periphery fixed both to said inside face and to said piece of flexible and porous material 28. The two parts which in this case are identical in shape and size are united by a close-outline peripheral junction line 30. They hold the piece of cotton wool captive between them. The two parts forming the walls of the pouch are united and the pouch is bonded to the inside face 25 of the part 13 by melting their materials by applying a hot tool having the shape of the junction line 30.

The two parts 13, 14 of flexible and leakproof material are also bonded to each other by a close-outline junction line 35 surrounding the location of the pouch. In order to facilitate application of the substance, the surface area of each part 13, 14 of the protective cover is significantly greater than that of the applicator 24 which is secured substantially in the center of the area defined by the junction line 35. The junction line 35 thus surrounds an area that is significantly greater than that occupied by the applicator. The junction line 35 is a line of weak adhesive or heat-sealing enabling the two parts 13 and 14 to be separated, i.e. they are suitable for peeling apart. Thus, certain laminates of metallized plastics material are designed specifically to be peelable-apart in this way.

By way of example, the part 13 to which the applicator is fixed can be made from a laminate comprising a 12 micrometer (μm) thick layer of polyethylene, a layer of metallization, and another layer of polyethylene (PE) that is 80 μm thick, thus enabling the parts to be peeled apart. The other part constituting the protective cover can be made from another, similar laminate. At least one of the two surfaces pressed one against the other is treated so as to make peeling apart possible after the close-outline junction line 35 has been made by applying a hot tool of corresponding shape against the two parts of leakproof material, and after the applicator has been fixed to one of them.

As shown, a fraction of the length of the junction line 35 extends at a distance from the facing edges of said two parts of flexible material 13, 14, thereby defining two pull tabs 36, 37 enabling said two parts to be separated. After being included in the protective cover, the applicator 24 is subjected to sterilization treatment by gamma rays.

The substance permanently wets the piece of cotton wool and the piece of porous material 28 inside the protective cover. To apply the substance, it suffices to open the protective cover 12 on at least three of its sides. The open cover makes it easier to handle the applicator 24 and makes it easier to use the substance available in the structure of the applicator (see FIG. 5).

Figure 6:
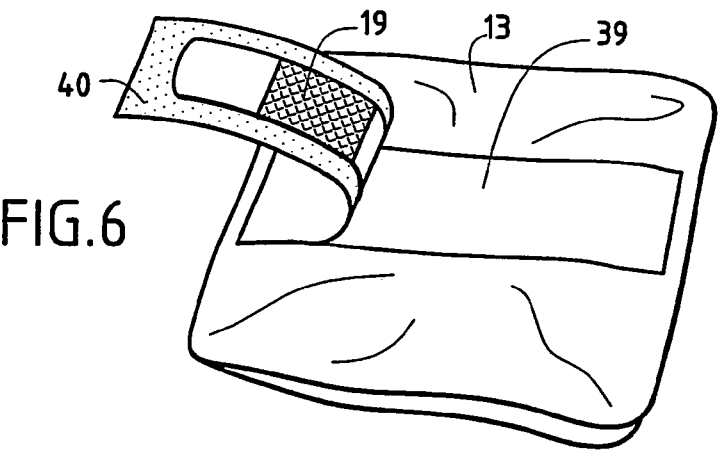
FIGS. 6 to 8 show the use of an adhesive dressing.
Figure 7:
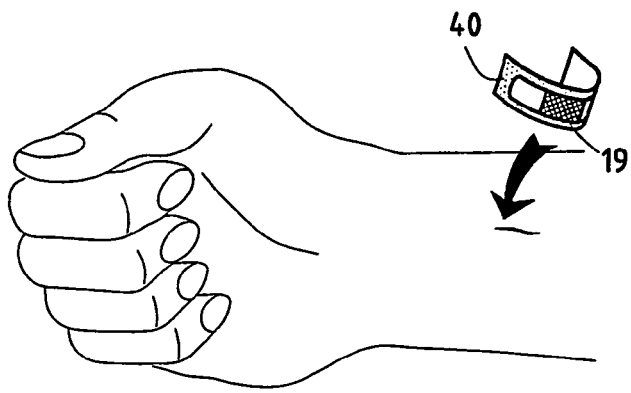
Figure 8:
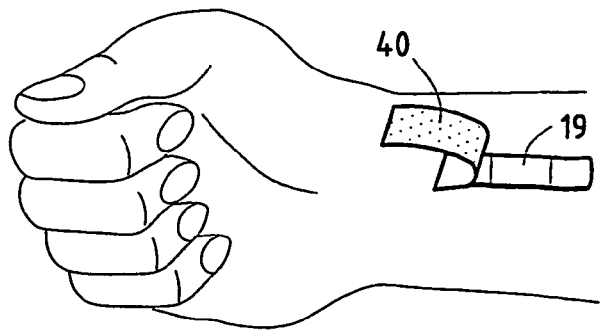

The peel-off cover 18 containing the adhesive dressing 19 is fixed via one of its face on an outside face of the protective cover 12. The inside portion 39 of the peel-off cover 18 which is fixed to the outside surface of the protective cover presents resistance to being torn off than is considerably greater than the force needed to open the peel-off cover. Consequently, the inside portion of the peel-off cover remains attached to said protective cover when the peel-off cover is opened to take hold of the dressing (see FIG. 6). However, the outside face of the dressing is weakly fixed (e.g. by moderate adhesive) to the inside face of the outside portion 40 of the peel-off cover which is not fixed to the protective cover. Consequently, when the peel-off cover is opened, the dressing 19 remains fixed to the portion 40 which is being pulled. Once the adhesive portions have been separated, the dressing can be applied (FIG. 7) by manipulating the detached portion of said peel-off cover, without any risk of touching the sterile zone. However, once applied to the skin, the adhesive zones of the dressing stick to the skin sufficiently strongly (FIG. 8) so that when the portion 40 of the peel-off cover is pulled away it becomes detached from the dressing. The sterilization treatment can be applied after the peel-off cover containing the dressing has been fixed to said protective cover containing the pouch.

The invention claimed is:

1. Single-use packaging for a liquid, semiliquid, or powder substance, the packaging comprising:
    a protective cover including two separable leakproof pieces of material, and
    an applicator enclosed in said protective cover, said applicator being fixed to an inside face of one of said leakproof pieces of material, said applicator forming a pouch holding captive material in which the substance is distributed, said pouch comprising:
        a piece of flexible and porous material fixed to said inside face,
        another piece of flexible material fixed at a periphery thereof both to said inside face and to said piece of flexible and porous material, and
        a material including cotton wool in which said substance is distributed, the material in which the substance is distributed being housed between said piece of flexible and porous material and said other piece of flexible material.

2. Packaging according to claim 1, wherein said leakproof pieces of said protective cover are flexible and are bonded together by a close-outline junction line surrounding a location of said applicator.

3. Packaging according to claim 2, wherein said junction line surrounds an area that is significantly greater than that occupied by said applicator, the applicator being situated substantially in the center of a surface defined by said junction line.

4. Packaging according to claim 2, wherein said junction line is one of:
    a line of low-strength adhesive and
    heat-sealing, enabling the two pieces of leakproof material to be separated by a "peel" effect.

5. Packaging according to claim 2, wherein said junction line extends over a fraction of a length thereof at a distance from facing edges of said two pieces of leakproof material so as to define pull tabs, enabling said two pieces to be separated.

6. Packaging according to claim 1, further comprising a peel-off cover containing an adhesive dressing, said peel-off cover having one face thereof fixed to an outside face of said protective cover.

7. Packaging according to claim 6, wherein an outside face of said dressing is weakly secured to an inside face of a portion of the peel-off cover which is not fixed to the protective cover.

8. Packaging according to claim 1, wherein the applicator is formed by at least one of:
    a fiber,
    a sponge, and
    a non-woven material.

* * * * *